US011171944B2

(12) United States Patent
Brown et al.

(10) Patent No.: US 11,171,944 B2
(45) Date of Patent: *Nov. 9, 2021

(54) SYSTEMS AND METHODS FOR SECURE AUTOMATED NETWORK ATTACHMENT

(71) Applicant: CABLE TELEVISION LABORATORIES, INC, Louisville, CO (US)

(72) Inventors: Ralph William Brown, Boulder, CO (US); Bernard McKibben, Golden, CO (US); Stuart Hoggan, Providence, UT (US); Brian A. Scriber, Lafayette, CO (US)

(73) Assignee: Cable Television Laboratories, Inc., Louisville, CO (US)

( * ) Notice: Subject to any disclaimer, the term of this patent is extended or adjusted under 35 U.S.C. 154(b) by 313 days.

This patent is subject to a terminal disclaimer.

(21) Appl. No.: 16/431,570

(22) Filed: Jun. 4, 2019

(65) Prior Publication Data

US 2019/0288997 A1    Sep. 19, 2019

Related U.S. Application Data

(63) Continuation of application No. 15/419,853, filed on Jan. 30, 2017, now Pat. No. 10,356,081.

(Continued)

(51) Int. Cl.
*H04L 29/06* (2006.01)
*H04W 76/10* (2018.01)
(Continued)

(52) U.S. Cl.
CPC ......... *H04L 63/0823* (2013.01); *G16H 40/20* (2018.01); *H04L 63/083* (2013.01);
(Continued)

(58) Field of Classification Search
CPC ... H04L 63/0823; H04L 63/083; G16H 40/20; G16H 40/67; H04W 76/10; H04W 12/0609; H04W 48/17; H04W 84/12
See application file for complete search history.

(56) References Cited

U.S. PATENT DOCUMENTS 6,304,974 B1 * 10/2001 Samar ................ H04L 63/0442
380/279
8,341,717 B1 * 12/2012 Delker .................... H04L 63/20
726/10

(Continued)

*Primary Examiner* — Shin-Hon (Eric) Chen
(74) *Attorney, Agent, or Firm* — Armstrong Teasdale LLP (57) ABSTRACT

A method for automatically attaching a purpose-built electronic device to a provider network includes steps of discovering, by a Wi-Fi module of the purpose-built electronic device, a wireless data network in operable communication with the provider network selecting, by the Wi-Fi module, the wireless data network, transmitting a primary authentication certificate from the Wi-Fi module to an authentication, authorization, and accounting server of the provider network, receiving, by an application server of the provider network, a secondary authentication certificate from a functionality module of the purpose-built electronic device authenticating, by the provider network, the primary and secondary authentication certificates, and attaching the purpose-built device to the provider network.

15 Claims, 3 Drawing Sheets

Related U.S. Application Data (60) Provisional application No. 62/288,535, filed on Jan. 29, 2016.

(51) Int. Cl.
    *G16H 40/20*        (2018.01)
    *H04W 48/00*      (2009.01)
    *H04W 12/06*      (2021.01)
    *H04W 84/12*      (2009.01)
    *G16H 40/67*       (2018.01)

(52) U.S. Cl.
    CPC ....... *H04W 12/0609* (2019.01); *H04W 48/17* (2013.01); *H04W 76/10* (2018.02); *G16H 40/67* (2018.01); *H04W 84/12* (2013.01)

(56) References Cited

U.S. PATENT DOCUMENTS

| | | | | |
|---|---|---|---|---|
| 8,793,490 B1* | 7/2014 | Szwalbenest | ....... | H04L 63/0853 713/168 |
| 8,929,521 B2* | 1/2015 | Beyer | ............... | H04M 3/382 379/93.02 |
| 2005/0148321 A1* | 7/2005 | Igarashi | ............... | H04L 63/102 455/411 |
| 2005/0172118 A1 | 8/2005 | Nasu | | |
| 2005/0204164 A1* | 9/2005 | Kakii | ............... | H04L 9/3268 726/5 |
| 2007/0055881 A1* | 3/2007 | Fuchs | ............... | H04L 9/3263 713/175 |
| 2007/0135866 A1* | 6/2007 | Baker | ............... | G06F 19/3418 607/60 |
| 2008/0120711 A1* | 5/2008 | Dispensa | ............ | H04L 63/08 726/7 |
| 2009/0028337 A1* | 1/2009 | Balabine | ............. | H04L 63/04 380/277 |
| 2009/0222902 A1* | 9/2009 | Bender | ............... | G06F 21/33 726/10 |
| 2011/0185183 A1* | 7/2011 | Yamamoto | ...... | H04L 63/0823 713/182 |
| 2011/0219227 A1* | 9/2011 | Sharif | ............... | G06F 21/33 713/158 |
| 2014/0031011 A1* | 1/2014 | West | ............... | H04W 12/08 455/411 |
| 2014/0359747 A1* | 12/2014 | Le | ............... | H04L 9/3297 726/10 |
| 2015/0134956 A1* | 5/2015 | Stachura | ............ | H04L 63/0807 713/168 |
| 2015/0237498 A1* | 8/2015 | Freedman | .......... | H04L 63/02 455/419 |
| 2015/0372825 A1* | 12/2015 | Park | ............... | H04W 12/0609 713/156 |
| 2016/0036794 A1* | 2/2016 | Adhya | ............... | H04W 12/06 726/4 |
| 2017/0005806 A1* | 1/2017 | Brand | ............... | H04L 9/3263 |
| 2019/0251765 A1* | 8/2019 | Masters | ............... | H04L 63/08 |

\* cited by examiner

SYSTEMS AND METHODS FOR SECURE AUTOMATED NETWORK ATTACHMENT

CROSS REFERENCE TO RELATED APPLICATIONS

This application is a continuation of U.S. application Ser. No. 15/419,853, filed Jan. 30, 2017, which claims the benefit of and priority to U.S. Provisional Patent Application Ser. No. 62/288,535, filed Jan. 29, 2016, both of which are incorporated herein by reference in their entireties.

BACKGROUND

The field of the disclosure relates generally to management of computer networks, and more particularly, to associating and provisioning wireless devices over such networks.

Some conventional Wi-Fi architectures utilize a Cloud for Mobile Interactive (C4MI) platform for networks employing an enterprise system. In a healthcare provider facility, such as a hospital or clinic, a wireless network implements a multi-layer network allowing different types of network traffic to be securely separated from each other on separate layers. For example, clinical data from medical devices is separated from enterprise data for management administration, and also is separated from guest or visitor data for Internet access traffic. The multiple network layers can further be segmented by frequency or channel to ensure sufficient bandwidth, quality of service, or reliability to support the applications using that network layer. The C4MI Wi-Fi platform may utilize a network geometric design layout, for example, a "Tholian Web" Wi-Fi geometric design/implementation. The geometric design and implementation of C4MI provides a foundation for placement of Wi-Fi access points (APs) and segregation of data traffic over the network (e.g., clinical, enterprise, guest, etc.).

A hotspot is a wireless local area network (LAN) node that provides Internet connection and virtual private network (VPN) access from a particular location for wireless devices with connectivity. Typically, a wireless device user manually connects to a hotspot by searching for visible wireless connection options, selecting one of the options, and then entering authentication information (e.g., a password) to connect. Wi-Fi Alliance (WFA) Passpoint™, also known as Hotspot 2.0™, or just "Passpoint," includes a set of protocols which allow a wireless device user to streamline network access in hotspots and eliminate the need to find and authenticate a network each time the device connects. A "Passpoint device" refers to an electronic device that passes certification testing based on WFA Hotspot 2.0. Passpoint includes certificate-based authentication mechanisms that provide automated network discovery and attachment on secured service set identifiers (SSIDs). Passpoint supports roaming within and across networks. Over-the-network device provisioning is accomplished with a standard WFA certified interface, and is based on the Access Network Query Protocol (ANQP).

Passpoint is used in a Wi-Fi network to select a wireless network SSID based on parameters such as 802.11 media access control (MAC) layer messages. Domain names or other identifiers, such as consortium ID, as well as preferred or excluded networks can also identify the wireless network. Additionally, network loading and available backhaul connectivity can be used for network selection decisions made by client devices. Devices utilizing Passpoint query Passpoint SSIDs for network roaming capabilities using 802.11 MAC layer messages. Wireless devices select an SSID based on one or a combination of (i) support for their provider realm (e.g., "@hospital.com"), (ii) supported consortium IDs (e.g., "HealthcareWiFi"), (iii) mobile network operator (MNO) identifiers, and (iv) SSID names, preferred or excluded. Network loading and available backhaul connectivity can also be used for network selection decisions. Passpoint does not presently though, provide device access across multiple tiers of a network. With wireless medical devices in particular, other networks (such as those not part of a particular or hospital network) may not be accessible by the wireless medical device. Accordingly, portable wireless medical devices may not be able to communicate through a wireless network outside of the particular clinical network for which they are configured.

BRIEF SUMMARY

In an embodiment, a method for automatically attaching a purpose-built electronic device to a provider network includes steps of discovering, by a Wi-Fi module of the purpose-built electronic device, a wireless data network in operable communication with the provider network selecting, by the Wi-Fi module, the wireless data network, transmitting a primary authentication certificate from the Wi-Fi module to an authentication, authorization, and accounting server of the provider network, receiving, by an application server of the provider network, a secondary authentication certificate from a functionality module of the purpose-built electronic device authenticating, by the provider network, the primary and secondary authentication certificates, and attaching the purpose-built device to the provider network.

In an embodiment, a system for automated attachment of wireless electronic devices, includes a first purpose-built electronic device and a provider subsystem. The first purpose-built electronic device includes a Wi-Fi module and a functionality module. The provider subsystem includes an authentication, authorization, and accounting server for verifying a primary authentication certificate from the Wi-Fi module, and an application server for verifying a secondary authentication certificate from the functionality module.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

Unless otherwise indicated, the drawings provided herein are meant to illustrate features of embodiments of this disclosure. These features are believed to be applicable in a wide variety of systems including one or more embodiments of this disclosure. As such, the drawings are not meant to include all conventional features known by those of ordinary skill in the art to be required for the practice of the embodiments disclosed herein.

DETAILED DESCRIPTION

In the following specification and claims, reference will be made to a number of terms, which shall be defined to have the following meanings.

The singular forms "a," "an," and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The embodiments herein describe and illustrate a system and method for secure, automated network discovery and attachment of a wireless device to a network, and particularly on multiple-layer, enterprise wireless networks, including without limitation, Wi-Fi networks. The embodiments described below are featured primarily in the context of healthcare providers and medical devices utilizing Wi-Fi networks. However, a person of ordinary skill in the art, after reading and comprehending the written disclosure and accompanying drawings, will understand how the principles described herein are applicable to enterprise environments in general which utilize wireless network technology.

The embodiments described herein further disclose how secure credentials, including without limitation, X.509 certificates, may be used for device authentication of both general purpose devices (e.g., smart phones, tablets, personal computers, etc.) and purpose-built devices (e.g., medical devices) which may not have user interface capability for making manual network selection and for manually entering credentials (such as username and password) for secure authentication. According to the embodiments herein, a particular automated network discovery and attachment scheme of a particular provider, such as a hospital/clinical setting, could be extended to remote locations, such as a medical patient's home, thereby providing the same level of secure automated network selection and attachment at the remote setting as may be realized in the provider network setting. Accordingly, irrespective of the wireless setting, purpose-built devices may avoid a sign-on process to automatically and securely attach to and be authenticated by the appropriate network (which may be remote from the AP of the particular device) without human intervention or requiring a user name and password.

In an exemplary embodiment, Passpoint is overlaid with a C4MI implementation to provide a robust security layer. Passpoint, for example, supports several types of security credentials. According to the embodiments disclosed herein, other wireless networks may use other types of security credentials, but may apply processes and schemes for secure, automated network attachment and authentication. Credential sets which may be compatible with Passpoint include, without limitation, device or user certificates, such as Extensible Authentication Protocol (EAP) and EAP Transport Layer Security (EAP-TLS), or a mutual authentication between network and device using certificate. EAP generally requires a certificate from a Certificate Authority (CA) for the device to certify the network.

User names with passwords can also be utilized with Passpoint as credential sets. In this example, the credential set may utilize, without limitation, EAP Tunneled Transport Layer Security (EAP-TTLS) with Microsoft Challenge Handshake Authentication Protocol version 2 (MSCHAPv2). EAP-TTLS provides authentication similar to EAP-TLS, but does not require that each user be issued a certificate. Instead, only the authentication servers are issued certificates. Such credential sets otherwise generally require a CA certificate for the device to certify the network. Utilization of these credential sets allow the system to mitigate "man-in-the-middle" attacks and malicious APs, and the device does not allow a user to bypass network authentication or accept an unknown CA certificate if compliant to Passpoint specifications. Other credentials supported by Passpoint include, without limitation, EAP-TTLS Password Authentication Protocol (PAP), Subscriber Identity Module (SIM) based credentials for mobile operators, such as EAP Subscriber Identity Module (EAP-SIM), EAP Authentication and Key Agreement (EAP-AKA), and EAP Authentication and Key Agreement prime (EAP-AKA').

Figure 1:
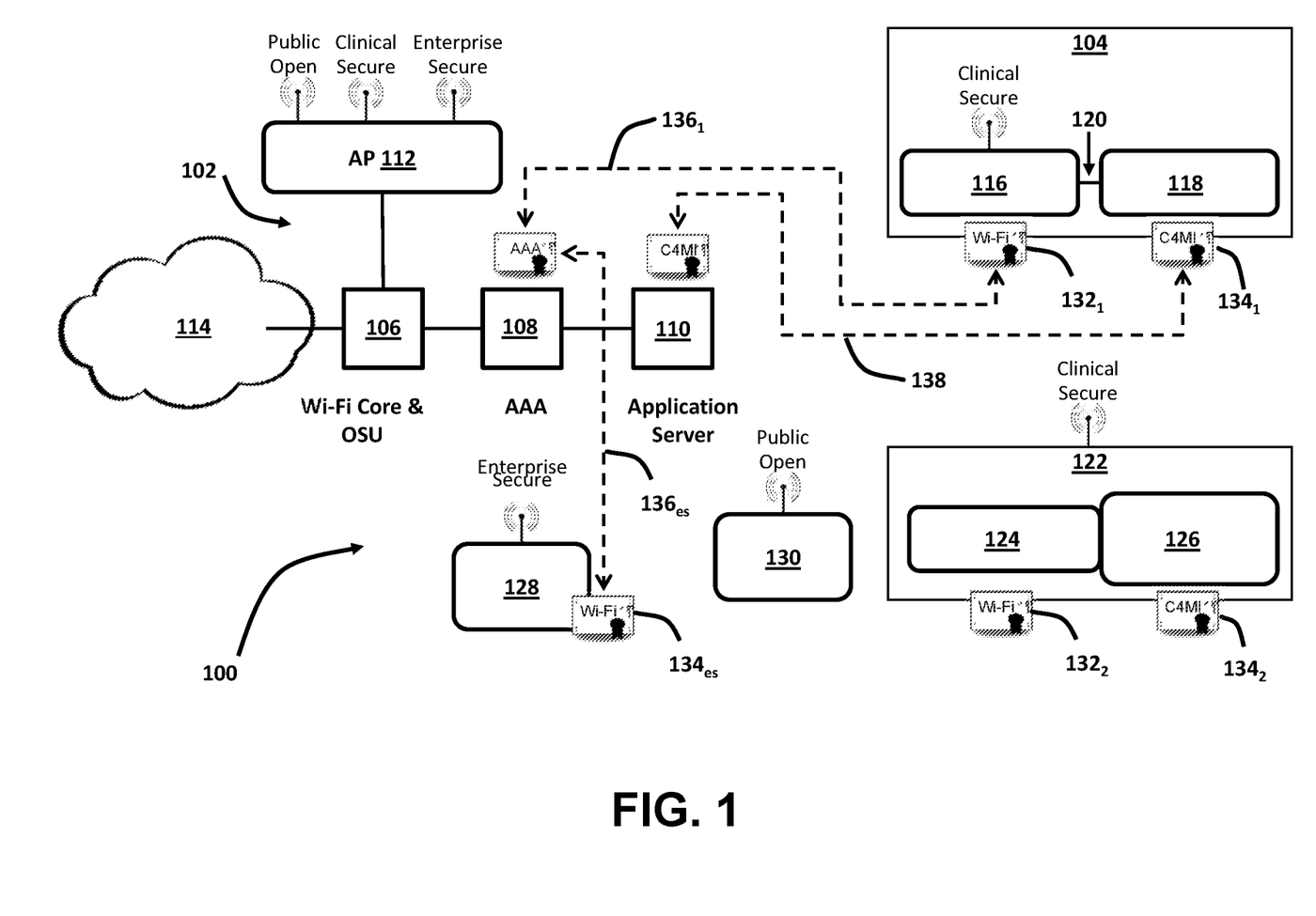
FIG. 1 is a schematic illustration of an exemplary network attachment system, according to an embodiment.

FIG. 1 is a schematic illustration of an exemplary network attachment system 100. System 100 includes a provider subsystem 102 to which a first electronic device 104 wirelessly connects. Provider subsystem 102 includes a Wi-Fi core unit 106 including a Hotspot 2.0 online signup (OSU), which is an open SSID giving the ability for wireless clients to connect to the secure hotspot service by signing up and downloading a custom profile. According to the example illustrated in FIG. 1, provider subsystem 102 represents a medical or clinical setting, and further includes an authentication, authorization, and accounting (AAA) server 108 and an application server 110. Wi-Fi core unit 106 communicatively connects with AAA server 108, an AP 112, and an electronic network 114. Electronic network 114 is, for example, the Internet, a Cloud-based network, or another form of electronic network, such as a LAN or WAN. AP 112 is, for example, configured to transmit and receive data over Public Open, Clinical Secure, and Enterprise Secure layers within provider subsystem 102. Communicative connections from Wi-Fi core unit 106 may be wireless, or wired, e.g., cable or Ethernet.

First electronic device 104 includes a first Wi-Fi module 116 and a first functionality module 118. As shown in the exemplary embodiment, first Wi-Fi module 116 represents a USB Wi-Fi module which communicates with functionality module 118 over an electrical connection 120, which is, for example, a USB, Ethernet, or compact flash connection or the equivalent. First functionality module 118 includes at least one processor (not shown) for executing the functions particular to first electronic device 104, and for transmitting/receiving electronic data to/from first Wi-Fi module 116 over electrical connection 120. In the exemplary embodiment, first electronic device 104 is a medical device located within the transmission range of AP 112 of provider subsystem 102, and first Wi-Fi module 116 wirelessly communicates with AP 112 at the Clinical Secure layer of provider subsystem 102, as described further below.

In an embodiment, system 100 further includes a second electronic device 122, having a second Wi-Fi module 124 and a second functionality module 126. In this example, second electronic device 122 is also a medical device, but differs from first electronic device 104 in that second Wi-Fi module 124 is integral to second electronic device 122. Second electronic device 122 is similarly located within the transmission range of provider subsystem 102 and wirelessly communicates with AP 112 at the Clinical Secure layer of provider subsystem 102. In an embodiment, system 100 further includes an enterprise Wi-Fi client 128 and a visitor Wi-Fi client 130. Both enterprise Wi-Fi client 128 and visitor Wi-Fi client 130 may represent, for example, electronic devices within the transmission range of provider subsystem 102, such as smart phones, tablets, personal computers, or other electronic devices capable of wirelessly connecting with AP 112. In this example, enterprise Wi-Fi client 128 wirelessly communicates with AP 112 at the Enterprise Secure layer, and visitor Wi-Fi client 130 wirelessly communicates with AP 112 at the Public Open layer.

In operation, network attachment system 100 implements a two-certificate attachment scheme for either or both of first and second electronic devices 104, 122. Medical devices, for example, differ in how they integrate Wi-Fi functionality. That is, a separate Wi-Fi module (e.g., first Wi-Fi module 116) with a standard interface, such as USB, Ethernet, compact flash, etc., is potentially removable, whereas an integral Wi-Fi module (e.g., second Wi-Fi module 124) may include an embedded Wi-Fi chip integrated into the device itself. According to the present embodiments, both architectures utilize two different certificates: (1) a Wi-Fi certificate 132 for the USB module or integral chip to secure network attachment and HS 2.0/Passpoint implementation; and (2) a medical device functionality certificate 134 to verify that the medical device (e.g., 104, 122) conforms to C4MI requirements for interoperability. In an exemplary embodiment, Wi-Fi certificate 132 is provisioned at manufacture of the particular electronic device. Alternatively, Wi-Fi certificate 132 is provisioned at the care provider (e.g., provider subsystem 102). In the exemplary embodiment, medical device functionality certificate 134 is installed at the time of manufacture of the particular device.

As shown in the exemplary embodiment, multiple layers (e.g., Public Open, Clinical Secure, Enterprise Secure, etc.) are used in a clinical or hospital setting. The two-certificate approach described herein though will be understood to be adaptable to different wireless networks or enterprises that support multiple network layers. As described herein, purpose-built devices, such as medical devices, have security credentials inserted into the device at the time of manufacture to provide a higher level of security. A trust authority can be used to issue these security credentials to further increase the security level. In contrast, general-purpose devices, such as smart phones, tablets, personal computers, etc., that are commercially available generally do not have application specific security credentials installed at the time of manufacture. These general-purpose devices may use an OSU process to provision the security credentials necessary for automatic network attachment. How and when particular security credentials are provisioned may be determined by the respective network/enterprise according to its own policies. The exemplary embodiments herein are described with respect to medical devices. However, the disclosed attachment and provisioning systems and methods are applicable to other purpose-built devices.

In the exemplary embodiment, general-purpose devices used by doctors or hospital staff (e.g., enterprise Wi-Fi client 128) are provisioned to enable an automatic attachment to the appropriate enterprise network (e.g., at AAA server 108) through a Passpoint/Hotspot 2.0 primary authentication 136. For automatic attachment, individuals are able to auto-attach wireless devices across work groups, campuses and partners of provider subsystem 102 through primary authentication 136. In this example, hospital administrators and/or management are also enterprise Wi-Fi client 128 devices, and follow a similar automatic attachment process by primary authentication 136, but may attach to a separate enterprise network, such as a second Enterprise Secure layer of provider subsystem 102. In the exemplary embodiment, visitor Wi-Fi clients 130 (i.e., general-purpose devices of visitors to the hospital of provider subsystem 102) would attach to a separate layer (e.g., Public Open layer) of subsystem 102, and would not be permitted to access any of the Clinical Secure or Enterprise Secure layers.

In an embodiment, network attachment system 100 is further configured to implement procedures regarding OSU of new authorized users, and device provisioning for new devices (e.g., tablets, smart phones, personal computers, etc.) of existing authorized users. An exemplary procedure for the embodiment shown in FIG. 1 may include one or more Passpoint SSIDs advertising an operator-friendly name (e.g., a care provider realm, a consortia ID, etc.) and OSU capabilities (e.g., of Wi-Fi core unit 106). After the operator-friendly name is presented to the user device, the user may select the operator name, and the device will associate to the OSU SSID and be directed to a provisioning server. A subscription is then created for new users, and the particular device is provisioned for secure SSID settings and an operator-driven network selection policy. Once the OSU process is complete, the user's device then performs network selection and attaches to the network. According to this procedure set, one operator cannot overwrite the subscription of another, and when multiple subscriptions are provisioned, the user is able to select a preferred operator.

With respect to Wi-Fi certificate 132 and medical device functionality certificate 134, network attachment system 100 may accommodate the implementations of two such sets of security credentials utilizing X.509 certificates, for example. Thus, Wi-Fi certificate 132 provides security credentials for the Wi-Fi network interface itself, whether separate or integrated, which secures the network selection and attachment, verifying the Passpoint implementation. Medical device functionality certificate 134 allows for a secondary authentication 138 of the medical device functionality (e.g., of functionality modules 118, 126) to the appropriate network server (e.g., application server 110) to validate that the medical device conforms to the required interoperability and security requirements (C4MI in this example). Secondary authentication 138 thus validates that the device functionality, separately from its Wi-Fi accessibility, is a trusted implementation. Secondary authentication 138 therefore provides a further preventative measure against attack on the network from a malicious device. In other words, in a clinical setting, the secondary authentication 138 advantageously assures that the device is a valid medical device and not a potential network attack from a general-purpose device or a compromised purpose-built device.

In an exemplary embodiment, in order to further raise the level of assurance, security credentials are issued from a trusted authority and properly installed into the devices, either at the point of manufacture or securely provisioned using standard provisioning interfaces. It may be necessary for purpose-built devices that have not yet been certified to place trust on the Wi-Fi module and certificate. In such an embodiment, some other attestable method may be used to verify the purpose-built device to which the module is attached or in which the module is embedded.

According to the exemplary embodiment illustrated in FIG. 1, a two-phase authentication process is implemented for one or more purpose-built devices (e.g., devices 104, 122). In the first phase of authentication, the respective Wi-Fi module (e.g., module 116, 124) attaches to the appropriate wireless network (e.g., the clinical data network of the Clinical Secure layer). In the second phase of authentication, the respective purpose-built functionality portion (e.g., module 118, 126) of the device authenticates with the appropriate data network server (e.g., application server 110) to verify that the device is a valid purpose-built device and operates properly with the data network, such as a medical device with a clinical network, or C4MI requirements in the exemplary system illustrated in FIG. 1.

In an alternative embodiment, secondary authentication 138 is not limited to only wireless connections, but may also be implemented with respect to wired connections, such as Ethernet. In one example, a medical device is connected to a clinical data network by Ethernet connection, and the two-phase authentication scheme, described above, is implemented. In the first phase, AAA server 108 utilizes Wi-Fi certificate 132 to authenticate the Wi-Fi module (e.g., module 116, 124) for access to the appropriate Wi-Fi network. In the second phase of authentication, the medical device functionality certificate 134 is authenticated by application server 110 using an appropriate protocol, for example, Protocol for Carrying Authentication for Network Access (PANA), Hypertext Transfer Protocol (HTTP) over TLS (HTTPS), or Internet Protocol Security (IPsec).

According to the embodiments described herein, network attachment system 100 is particularly advantageous to health care networks or clinical settings using layered wireless communications. According to the embodiment illustrated in FIG. 1, Passpoint/Hotspot 2.0 is implemented together with C4MI and/or TLS mutual authentication to create a multi-tiered secured network having Wi-Fi access available to not only medical devices, but also devices of health care specialists, administration and management devices, and open SSID visitor networks with sign-in portals. According to the embodiment of FIG. 1, AP 112 may advantageously support multiple Passpoint-enabled SSIDs to securely separate traffic among the several user groups. Consumer devices, such as tablets and smart phones, are able to utilize the Passpoint OSU for provisioning of credentials and network selection (e.g., through primary authentication 136), and medical device vendors are able to insert functionality certificates at the time of manufacturing for higher security and automatic attachment (e.g., through both primary authentication 136 and secondary authentication 138) without requiring OSU. The two-phase approach thus advantageously allows the purpose-built devices to automatically attach and roam among access points without required user intervention. In an exemplary embodiment, primary authentication 136 is a Passpoint/Hotspot 2.0 authentication, and secondary authentication 138 is a TLS mutual authentication.

Systems and methods according to the embodiment illustrated in FIG. 1 present a unique system architecture which allows a care provider's AP (e.g., AP 112) to "advertise" three or more types of wireless networks, that is, an open public network for visitors, a secure clinical data network for medical devices, and a secure enterprise network for the enterprise applications. In some embodiments, the plurality of access points may be deployed to cover a large provider subsystem (e.g., a C4MI network geometric design layout), and to enable connection to the core Wi-Fi network (e.g., Wi-Fi core unit 106) and its associated OSU server. A medical device application server (e.g. application server 110) is connected to the enterprise network, and the enterprise network is also attached to the Internet (e.g., electronic network 114). As illustrated in FIG. 1, at least four types of clients may access system 100: enterprise Wi-Fi client 128 that uses Passpoint to attach to the secure enterprise network; visitor Wi-Fi client 130 that uses the open public network for Internet access while visiting the facility; and at least two medical devices (e.g., 104, 122) that connect to the secure clinical data network with the second set of security credentials (e.g. medical device functionality certificate 134) for authentication as valid medical devices.

This novel approach is of particular value with respect to medical devices being utilized by patients who are often unable to manage an OSU process. A medical device, for example, may be configured to access a particular clinical network, but will often be unable to access a different network without first going through some level of setup by a skilled technician, even though different networks may be able to recognize the presence of the medical device, including push information transmitted by the device. Conventional single-tiered networks require each type of device (e.g., visitor, enterprise, purpose-built) to separately be provisioned, select, and attach to the particular network layer (e.g., Public Open, Enterprise Secure, Clinical Secure) in which that device operates. The two-phase authentication scheme described herein advantageously creates a multi-tiered secure network with Wi-Fi access available to the various devices without compromising the security of a purpose-built device from the network, or the network from an unauthenticated device.

Figure 2:
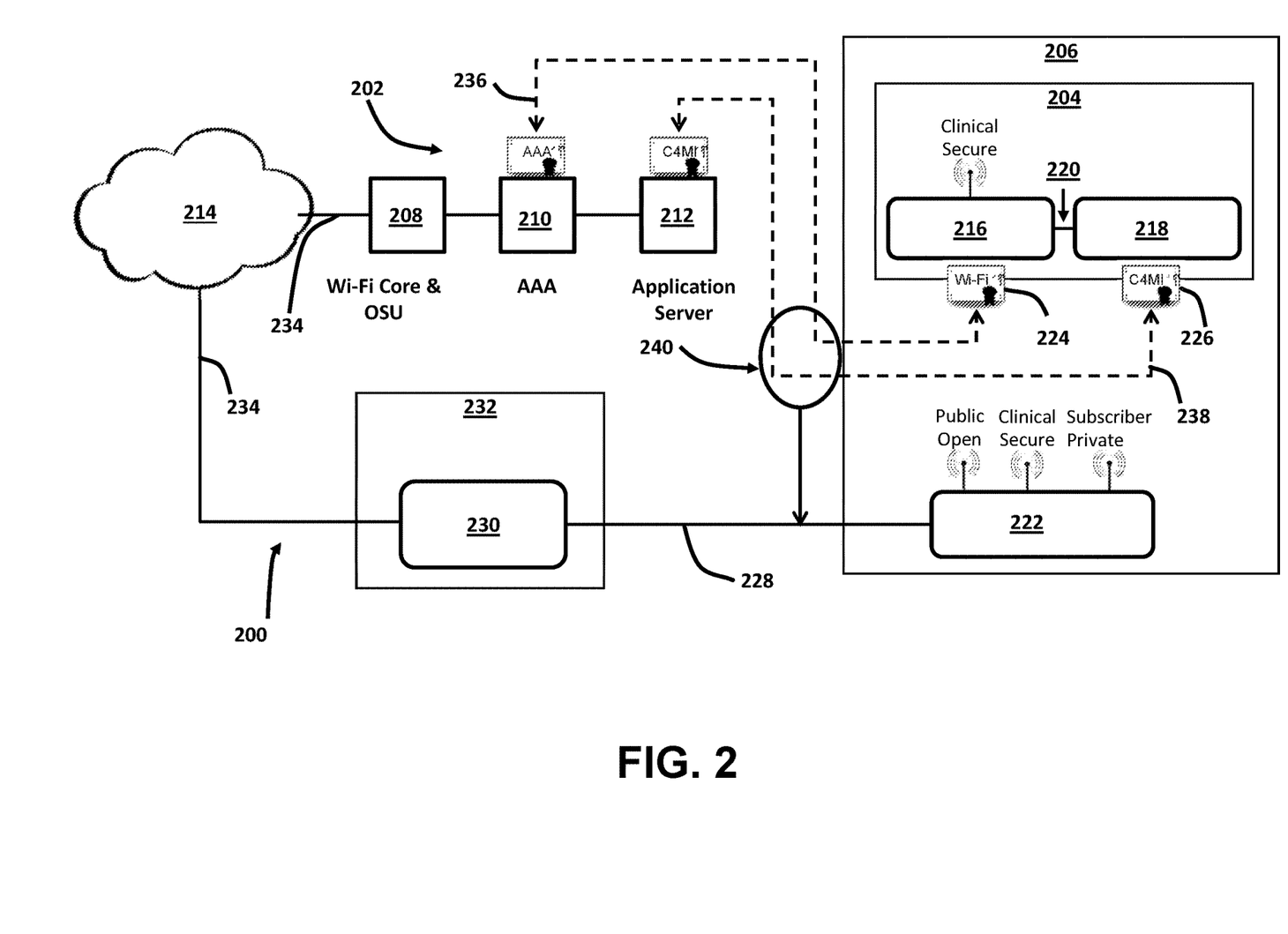
FIG. 2 is a schematic illustration of an alternative network attachment system, according to an embodiment.

FIG. 2 is a schematic illustration of an alternative network attachment system 200. Similar to system 100, described above, system 200 includes a provider subsystem 202, to which an electronic device 204 wirelessly connects. System 200 differs from system 100 in that electronic device 204 is located at a remote setting 206, such as a subscriber or patient home.

Provider subsystem 202 includes a Wi-Fi core unit 208 including a Hotspot 2.0 OSU, an AAA server 210, and an application server to 212. Wi-Fi core unit 208 communicatively connects with at least AAA server 210 and an electronic network 214, which is, for example, the Internet, a Cloud-based network, a LAN, or WAN. Provider subsystem 202 may further include an AP (not shown). Communicative connections from Wi-Fi core unit 208 may be wireless, or wired, e.g., cable or Ethernet. Electronic device 204 includes a Wi-Fi module 216 and a functionality module 218. As illustrated in FIG. 2, Wi-Fi module 216 is a USB Wi-Fi module, and communicates with functionality module 218 over an electrical connection 220. Wi-Fi module 216 is alternatively integrally configured with the architecture of functionality module 218, as described above with respect to FIG. 1 (second electronic device 122). Functionality module 218 includes at least one processor (not shown) for executing the functions particular to electronic device 204, and for transmitting/receiving electronic data to/from first Wi-Fi module 216 over electrical connection 120.

In an embodiment, remote setting 206 further includes a wireless gateway device 222, which is, for example, a cable wireless gateway available at a cable subscriber's home location. Wireless gateway device 222 thus serves to function as a virtualized AP from which electronic device 204 is thereby able to access a Public Open layer or network, a desired Clinical Secure layer or network, and a Subscriber Private layer or network.

In operation, network attachment system 200 implements a two-certificate attachment scheme for electronic device 204, similar to that described above with respect to system 100 (FIG. 1), except for the remote operation of electronic device 204. This two-certificate attachment scheme includes: (1) a Wi-Fi certificate 224 for Wi-Fi module 216 to secure network attachment and HS 2.0/Passpoint implementation; and (2) a device functionality certificate 226 to verify that electronic device 204 conforms, for example, to C4MI requirements for interoperability. In an exemplary embodiment, Wi-Fi certificate 224 is provisioned at manufacture of electronic device 204. Alternatively, Wi-Fi certificate 224 is provisioned at provider subsystem 202. In the exemplary embodiment, device functionality certificate 226 is installed at the time of manufacture of electronic device 204.

In further operation, wireless gateway device 222 of network attachment system 200 connects with and communicates over a secure access network 228, which is, for example, a cable access network. In an exemplary embodiment, secure access network 228 communicates with an access network termination 230 of an operator headend 232, which itself is configured to communicate with electronic network 214 over a secure VPN 234. In an exemplary embodiment, electronic device 204 is provisioned to enable an automatic attachment to the appropriate layer/network (e.g., Clinical Secure) of AAA server 210 by a primary authentication 236 of Wi-Fi module 216 and a secondary authentication 238 of functionality module 218, without requiring an OSU process, and without risking unauthorized access to other layers of provider subsystem 202. In the exemplary embodiment, Wi-Fi certificate 224 and device functionality certificate 226, utilize X.509 protocols, and primary authentication 236 is a Passpoint/Hotspot 2.0 authentication process, and secondary authentication 238 is a TLS mutual authentication process. Primary authentication 236 and secondary authentication 238 are transmitted 240, for example, over secure VPN 234.

System 200 therefore implements a similar method to system 100 for secure automated network selection and attachment of a purpose-built device located in a remote setting from a provider subsystem. In the example illustrated in FIG. 2, the remote setting (e.g., remote setting 206) is the home of a cable subscriber patient, and a cable operator (e.g., operator headend 232) is the access network provider (e.g., secure access network 228) to the subscriber's home. Alternatively, different types of wired access (e.g., Digital Subscriber Line (DSL), fiber, etc.) or wireless access (e.g., Long-Term Evolution (LTE)) network providers may serve as the access network provider for system 200. In this example, the cable operator/access network provider provisions a wireless gateway in the subscriber's home with the same secure clinical data network identifiers as used in the AP of the provider subsystem. The access network provider provisions a secure VPN (e.g., secure VPN 234) connection from the gateway (e.g., wireless gateway device 222) to the care provider's enterprise networks through a regional network (e.g., electronic network 14). The medical device (e.g., electronic device 204) may then attach to the clinical data network using the same process that is used within the transmission range of the provider subsystem.

According to the embodiment illustrated in FIG. 2, an access network provider may further provision additional wireless networks in the wireless gateway to support the subscriber's private Internet/electronic network access, including a public network for community Internet access, and the open public network in the care provider's facilities. Alternatively, or additionally, multiple access network providers may be utilized in system 200 without departing from the scope of the embodiment. For example, a hospital may have multiple redundant Internet providers, permitting a neutral hosting of multiple network operators through the hospital's wireless network. Subscribers of these network operators could then seamlessly roam onto the wireless network, for example, using Passpoint roaming capabilities, without compromising the security of different devices among the multi-tiered architecture of the provider subsystem.

In some embodiments involving home deployments purpose-built devices, when implemented according to the 802.11-2012 specification, standard 802.11 MAC signaling protocols support only one security paradigm per SSID. Accordingly, multiple SSIDs may be implemented to allow a combination of open and Passpoint, or PSK and Passpoint, security paradigms. In other embodiments, reserved vendor proprietary fields are utilized to construct an equivalent scheme, which is then either standardized, or involves vendor proprietary procedures at the device and AP. In an alternative embodiment, at least three SSIDs are used to separate traffic according to the standard 802.11 MAC, without vendor proprietary signaling for open public SSIDs for guests, clinical SSIDs via Passpoint for certified medical devices, and subscriber private SSIDs via PSK for the subscriber. In at least one embodiment utilizing two SSIDs, a single Passpoint SSID, for both the subscriber private network and clinical network, may be utilized in addition to utilization of virtual AP schemes to separate and forward traffic. In another embodiment, a single Passpoint SSID for the public and clinical networks is utilized for cable multiple-system operators (MSO) Wi-Fi architecture or virtual AP.

Figure 3:
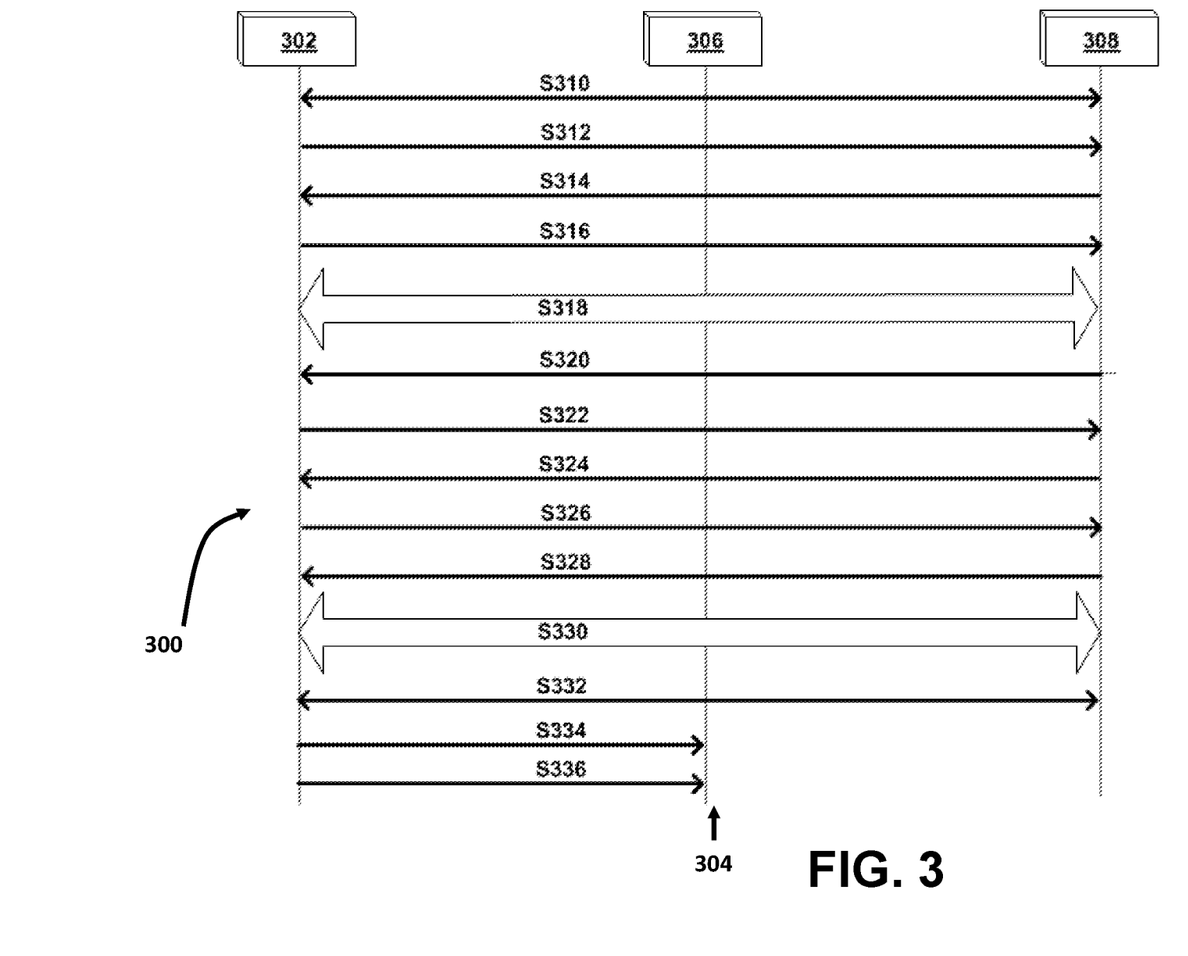
FIG. 3 illustrates an exemplary flow process for device provisioning, according to an embodiment.

FIG. 3 illustrates an exemplary flow process 300 for provisioning of a wireless electronic device 302, which may be implemented with systems 100 and 200, described above. Process 300 illustrates a message exchange sequence 304 for provisioning username and password credentials to wireless electronic device 302 using Security Policy Protocol (SPP), for example, by way of an AP 306 in communication with an OSU server 308. Process 300 begins at step S310. In step S310, wireless electronic device 302 initiates a TLS connection to OSU server 308. In an exemplary embodiment, step S310 is performed utilizing server-side authentication using HTTPS. In an alternative embodiment, separate Transmission Control Protocol (TCP) connections (and TLS sessions) can be used for Simple Object Access Protocol (SOAP) eXtensible Markup Language (XML) exchanges that happen prior to and after the user interaction via a web browser.

In step S312, wireless electronic device 302 transmits, for example, sppPostDevData SOAP method to OSU server 308, which includes Devinfo and DevDetail MOs, and which may further include SessionID, requestReason, and redirectURI information. In an exemplary embodiment, a value for requestReason is set to "Subscription registration," indicating the desire to register for credentials. The redirectURI information is generated by wireless electronic device 302, which resolves to a resource internal in the mobile device. After OSU server 308 has received sufficient data to complete the registration process, OSU server 308 redirects a web browser of wireless electronic device 302 to the redirectURI (see step S320, below). An internal event caused by retrieval of the redirectURI resource can then be used to signal to a connection manager (not shown) of wireless electronic device 302 that the registration process is complete and to proceed to step S314.

In step S314, OSU server 308 transmits a SOAP method sppPostDevDataResponse, including a sessionID value generated by OSU server 308 to wireless electronic device 302. In an exemplary embodiment, the sessionID is a 128-bit random number used to bind together messages from a specific mobile device to OSU server 308. The generated sessionID value may then be used in all subsequent SOAP messages exchanged within flow process 300. Once the user has signaled for subscription registration, OSU server 308 returns a command for wireless electronic device 302 to launch a browser (not shown) to the URI supplied in the message. In this example, the URI contains the generated sessionID value from the SOAP method's sessionID attribute. In an exemplary embodiment, the length of the sessionID is set to minimize the possibility an attacker could successfully guess the sessionID value and disrupt or break the provisioning process or steal the credentials of another wireless electronic device.

In step S316, wireless electronic device 302 transmits an HTTPS GET request to the URI provided in the sppPostDevDataResponse. In step S318, a user provides relevant subscription information to OSU server 308 (and selects a rate plan, if applicable). In step S320, after the exchange of registration data, OSU server 308 transmits a final HTTP 302 REDIRECT message to wireless electronic device 302. In step S322, wireless electronic device 302 transmits a sppPostDevData message to OSU server 308 containing the sessionID and requestReason. In an exemplary embodiment, the requestReason is set to "User input completed." According to this example, the sessionID further advantageously facilitates the use of multiple TLS tunnels and/or TCP connections between a particular wireless electronic device and OSU server 308. For implementation reasons, a mobile device may use more than one TLS tunnel and/or more than one TCP connection throughout the message flow sequence.

In step S324, OSU server 308 transmits to wireless electronic device 302 a sppPostDevDataResponse message. The sppPostDevDataResponse includes the sessionID, an addMO command, and a PerProviderSubscription MO. In step S326, after wireless electronic device 302 successfully adds the PerProviderSubscription MO (and other MOs, if present) to its management tree, wireless electronic device 302 transmits to OSU server 308 an sppUpdateResponse SOAP method containing the sessionID and the sppStatus set to "OK." In an embodiment, in the case where wireless electronic device 302 is not able to add the PerProviderSubscription MO (or other MOs, if applicable), wireless electronic device 302 transmits to OSU server 308 an sppUpdateResponse message with sppStatus set to "Error occurred," and may further transmit an Error Code, and wireless electronic device 302 deems credential provisioning to have failed and does not attempt to use any credential which may have been received during the message sequence illustrated in FIG. 3. Otherwise, flow process 300 then proceeds to step S328.

In step S328, OSU server 308 transmits to wireless electronic device 302 a sppExchangeComplete SOAP method containing the sessionID with sppStatus set to "Exchange complete, release TLS connection." In step S330, wireless electronic device 302 utilizes HTTPS to retrieve trust anchor CA certificates for the AAA server (e.g., AAA server 108, FIG. 1), a subscription remediation server, and a policy server (if applicable) using CertURLs in the PPS MO. In step S332, wireless electronic device 302 releases the TLS session established in step S310. In step S334, wireless electronic device 302 disassociates from AP 306, and in step S336, re-associates with AP 306 using newly established credentials, if available.

In an exemplary embodiment of flow process 300, and individual care provider subsystem (e.g., through OSU server 308) establishes network selection policies and provisions certificates to wireless electronic device 302 (e.g., a smart phone, tablet, personal computer, etc.), as well as available Wi-Fi modules (e.g., 116, 124, 216). In some embodiments, alternative WFA interfaces are available for device management, including, without limitation, Open Mobile Alliance Device Management (OMA-DM) and SOAP XML. Exemplary provisioning for wireless electronic device 302 may include, without limitation, non-SIM credentials, such as Wi-Fi and C4MI certificates or CA certificates, SSID settings, and or operator policies for network selection In some embodiments of flow process 300, Wi-Fi provisioning and data model parameters include subscription definitions and network selection criteria per subscription. A subscription definition may include, without limitation: credentials such as a username and password, a SIM, or a device certificate; an authentication protocol, such as EAP-SIM, EAP-AKA, EAP-AKA', EAP-TLS, or EAP-TTLS with MSCHAPv2, PAP, or Generic Token Card (GTC); Wi-Fi Protected Access 2 (WPA2) Anonymous identity; a CA certificate; a subscription duration, including an expiration date, a time usage limit, and/or a volume usage limit; and a subscription priority. Network selection criteria may include, without limitation: a home network fully qualified domain name (FQDN); a prioritized preferred roaming partner list by realm or mobile network operator (MNO) identifier, such as mobile country code (MCC) and/or mobile network code (MNC); a consortium ID; a preferred SSID; and excluded SSID; a minimum backhaul threshold; and a maximum basic service set (BSS) load threshold. According to the exemplary embodiments herein, the present systems and methods advantageously allow a network operator to push device provisioning, including credentials, over a standard Passpoint interface.

The present systems and methods further allow for improved interoperability of multiple general-purpose and purpose-built devices across a multi-tiered network structure, by implementing a novel two-phase authentication scheme utilizing C4MI devices security specifications with Passpoint 2.0 certificate based authentications. Such C4MI devices security specifications may include, without limitation, X.509 devices certificate profiles, X.509 user certificate profiles, a Public Key Infrastructure (PKI) hierarchy identifying a chain of trust, secure software download requirements for medical devices, and/or secure certificate injection requirements on medical device manufacturers. Present systems and methods further advantageously provide for improved PKI management, including, without limitation, processes for certifying that particular purpose-built devices comply with C4MI specifications, a certification board for setting security policies and making pass/fail decisions, a trusted certificate issuance system from third-party providers, and active PKI monitoring and policing against compromises or attacks.

Exemplary embodiments of automated network attachment systems and methods are described above in detail, and more particularly with regard to two-phase device authentication for wireless devices. The systems and methods of this disclosure though, are not limited to only the specific embodiments described herein, but rather, the components and/or steps of their implementation may be utilized independently and separately from other components and/or steps described herein.

Although specific features of various embodiments of the disclosure may be shown in some drawings and not in others, this convention is for convenience purposes and ease of description only. In accordance with the principles of the disclosure, a particular feature shown in a drawing may be referenced and/or claimed in combination with features of the other drawings.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a field programmable gate array (FPGA), a digital signal processing (DSP) device, and/or any other circuit or processor capable of executing the functions described herein. The processes described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term "processor."

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for automatically attaching a first electronic device operating at a first location to a provider network operating at a second location, the method comprising the steps of:
   discovering, by a communication module of the first electronic device, a communication data network in operable communication with the provider network;
   selecting, via the communication module, the communication data network;
   transmitting a primary authentication certificate from the communication module to an authentication server of the provider network;
   receiving, by an application server of the provider network, a secondary authentication certificate from a functionality module associated with the first electronic device;
   authenticating, by the provider network, the primary and secondary authentication certificates; and
   attaching the first device to the provider network,
   wherein the first location is one of (i) within an operational vicinity of the provider network at the second location, and (ii) outside of the operational vicinity of the provider network.

2. The method of claim 1, wherein the first device is a medical device and the provider network is associated with a clinical network.

3. The method of claim 2, wherein the step of attaching comprises attaching the medical device to a clinical secure layer of the provider network.

4. The method of claim 3, further comprising the step of provisioning an enterprise client device to an enterprise secure layer of the provider network.

5. The method of claim 4, wherein the step of provisioning comprises transmitting a primary authentication from the enterprise client device to the authentication server of the provider network.

6. The method of claim 4, wherein the enterprise client device is a general-purpose electronic device.

7. The method of claim 1, further comprising the step of provisioning a wireless visitor device to a public open layer of the provider network.

8. The method of claim 7, wherein the wireless visitor device is a general-purpose electronic device.

9. The method of claim 1, wherein the primary authentication certificate is based on an access network query protocol.

10. The method of claim 1, wherein the secondary authentication certificate is based on a cloud for mobile interaction platform.

11. The method of claim 10, wherein the secondary authentication certificate is received separately from the primary authentication certificate.

12. The method of claim 11, wherein the secondary authentication certificate is received over an Ethernet connection.

13. The method of claim 1, wherein the primary and secondary authentication certificates are received over one or more of a secure access network and a secure virtual private network.

14. The method of claim 1, wherein the communication data network is a wireless network.

15. The method of claim 14, wherein the wireless network is a Wi-Fi network.

\* \* \* \* \*